US011213484B2

(12) United States Patent
Zhang (10) Patent No.: US 11,213,484 B2
(45) Date of Patent: Jan. 4, 2022

(54) DIPIVEFRIN ORALLY DISINTEGRATING TABLET FORMULATIONS

(71) Applicant: INSIGNIS THERAPEUTICS, INC., North Haven, CT (US)

(72) Inventor: Mingbao Zhang, Millwood, NY (US)

(73) Assignee: INSIGNIS THERAPEUTICS, INC., North Haven, CT (US)

(*) Notice: Subject to any disclaimer, the term of this patent is extended or adjusted under 35 U.S.C. 154(b) by 0 days.

(21) Appl. No.: 16/803,432

(22) Filed: Feb. 27, 2020

(65) Prior Publication Data

US 2020/0276114 A1    Sep. 3, 2020

Related U.S. Application Data

(60) Provisional application No. 62/812,540, filed on Mar. 1, 2019.

(51) Int. Cl.
*A61K 9/00*        (2006.01)
*A61K 31/137*      (2006.01)
*A61K 31/216*      (2006.01)

(52) U.S. Cl.
CPC .......... *A61K 9/0056* (2013.01); *A61K 31/137* (2013.01); *A61K 31/216* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 3,809,714 | A | 5/1974 | Hussain et al. |
| 3,839,584 | A | 10/1974 | Hussain et al. |
| 4,094,983 | A | 6/1978 | Bodor |
| 4,180,586 | A | 12/1979 | Eriksen |
| 5,567,439 | A | 10/1996 | Myers et al. |
| 5,622,716 | A | 4/1997 | Barth |
| 5,622,717 | A | 4/1997 | Fuisz |
| 5,654,003 | A | 8/1997 | Fuisz et al. |
| 5,871,781 | A | 2/1999 | Myers et al. |
| 5,925,682 | A | 7/1999 | Gruber et al. |
| 6,596,298 | B2 | 7/2003 | Leung et al. |
| 6,923,981 | B2 | 8/2005 | Leung et al. |
| 7,025,983 | B2 | 4/2006 | Leung et al. |
| 7,067,116 | B1 | 6/2006 | Bess et al. |
| 9,877,921 | B2 | 1/2018 | Rawas-Qalaji et al. |
| 2003/0180357 | A1* | 9/2003 | Martino ............. A61K 9/286 424/465 |
| 2003/0235617 | A1 | 12/2003 | Martino et al. |
| 2004/0247648 | A1 | 12/2004 | Fadden et al. |
| 2005/0003467 | A1 | 1/2005 | Hori |
| 2007/0202163 | A1 | 8/2007 | Rawas-Qalaji et al. |
| 2015/0005356 | A1 | 1/2015 | Fleming |
| 2015/0164827 | A1 | 6/2015 | Rawas-Qalaji et al. |
| 2016/0220489 | A1 | 8/2016 | Fleming et al. |
| 2017/0020827 | A1 | 1/2017 | Rawas-Qalaji et al. |
| 2018/0147145 | A1 | 5/2018 | Rawas-Qalaji et al. |
| 2019/0076378 | A1 | 3/2019 | Zhang |

FOREIGN PATENT DOCUMENTS

| | | | |
|---|---|---|---|
| CN | 106109459 A | * 11/2016 | ........... A61K 31/352 |
| EP | 0159237 B1 | 5/1988 | |
| EP | 2085071 A1 | 8/2009 | |
| WO | 2007028247 A1 | 3/2007 | |
| WO | 2007143676 A2 | 12/2007 | |
| WO | 2018089570 A1 | 5/2018 | |
| WO | 2018191793 A1 | 10/2018 | |
| WO | 2019051387 A1 | 3/2019 | |

OTHER PUBLICATIONS

Rowntree, Journal of Pharmacology and Experimental Therapeutics (1924), 23, pp. 135-136.*
Tedeschi et al., Expert Review of Clinical Immunology (2008), 4(6), pp. 767-776.*
Rawas-Qalaji et al., Biopharmaceutics & Drug Disposition (2006), 27, pp. 427-435.*
International Search Report; International Application No. PCT/US2018/050223; International Filing Date—Sep. 10, 2018; dated Nov. 30, 2018.
Written Opinion; International Application No. PCT/US2018/050223; International Filing Date—Sep. 10, 2018 dated Nov. 30, 2018.
International Search Report; International Application No. PCT/US2020/020117; International Filing Date—Feb. 27, 2020; dated May 25, 2020.
Rachid Ousama et al., "Epinephrine (Adrenaline) Absorption from New-Generation, Taste-Masked Sublingual Tablets: A Preclinical Study," Journal of Allergy and Clinical Immunology; (Jan. 2013), vol. 131, No. 1, pp. 236-238, XP9520358.
Written Opinion of the International Searching Authority; International Application No. PCT/US2020/020117; International Filing Date—Feb. 27, 2020; dated May 25, 2020.
"Formulation and Diffusion of Epinephrine's Prodrug for Anaphylaxis Treatment," NSU Home, Academic Affairs, 2013-2014 Winners; (nova.edu), https://www.nova.edu/academic-affairs/faculty-research-grant/winners1314/formulation-diffusion-epinephrines-prodrug.html; 3 pages.
Allen, "Rapid-Dissolve Technology," International Journal of Pharmaceutical Compounding, (2003),vol. 7, (No. 6), pp. 449-450.
Aurora et al., "Oral Disintegrating Technologies," Drug Delivery Technoloogy, (2005), vol. 5., (No. 3), pp. 50-54.

(Continued)

*Primary Examiner* — Brian J Davis
(74) *Attorney, Agent, or Firm* — Cantor Colburn LLP (57) ABSTRACT

This disclosure provides orally disintegrating dipivefrin tablet (ODT) formulations, including ODT formulations containing L-dipivefrin HCl. The ODT formulations of the disclosure include 10 to 70% binder (wt %), 5 to 50% matrix former (wt %), and 1 to 20% taste masking agent (wt %). The ODT formulations of the disclosure rapidly provide epinephrine to a patient when administered. The disclosure also provides a method of treating a patient who has a condition responsive to epinephrine such as a cardiac event, asthma, croup, cancer, a microbial infection, Addison's disease, or an allergic reaction, particularly anaphylaxis by administering an orally disintegrating dipivefrin tablet formulations to the patient.

21 Claims, 2 Drawing Sheets

(56) References Cited

OTHER PUBLICATIONS

Bahar et al. "Species Difference of Esterase Expression and Hydrolase Activity in Plasma," Journal of Pharmaceutical Sciences, (2012) vol. 101, (No. 10), pp. 3979-3988.

Chang et al., "Fast-Dissolving Tablets," Pharmaceutical Technology, (2000), (No. 24), pp. 53-58.

Dobetti, "Fast-Melting Tablets: Developments and Technologies," Pharmaceutical Technology Drug Delivery, Europe 12, (2001), pp. 44-50.

Eisenburger et al., "Comparative Pharmacological Study on D, 1-Adrenaline Dipivalate Hydrochloride and 1-Adrenaline Hydrochloride After Local and Oral Administration," German Article, Klinge Pharma GmbH & Co., (2019), 37 pages.

Hamilton et al., "Orally Disintegrating Tablets, Advanced Orally Disintegratring Tablets Bring Significant Benefits to Patients and Product Life Cycles," Drug Delivery Technology, (2005), vol. 5, (No. 1), pp. 34-37.

Jerzsele, "Comparative Veterinary Pharmacokinetics," In book: Readings in Advanced Pharmacokinetics—Theory, Methods and Applications, Apr. 20, 2011; pp. 179-198.

Langer, "New Methods of Drug Delivery," Science, (1990), vol. 249, pp. 1527-1533.

Parakh et al., "A Review of Mouth Dissolving Tablet Technologies," Pharmaceutical Technology, (2003), (No. 27), pp. 92-98.

Sastry et al., "Process Development and Scale-Up of Oral Fast-Dissolving Tablets," In Drug Delivery to the Oral Cavity, CRC Press, Boca Raton, (2005), pp. 311-316.

Simons, K.J. et al., "Sublingual Epinephrine Adminislation in Humans: A Preliminary Study," J. of Allergy and Clin. Immunol., (Feb. 2004) 113, S260 Abstracts.

Verma et al., "Current Status of Drug Delivery Technologies and Future Directions," Pharmaceutical Technology On-Line, (2001), (No. 25)(2), pp. 1-14.

Anderson et al., "Site of Ocular Hydrolysis of a Prodrug, Dipivefrin, and a Comparison of its Ocular Metabolism with that of the Parent Compound, Epinephrine," Association for Res. in Vis. and Ophthal., Inc., (1980), vol. 19, (No. 7), pp. 817-823.

Wenninger, "The Oral Administration of Epinephrine," (1927), Arch. Internal Medicine (Chic)I, vol. 40, No. (5); pp. 701-714.

* cited by examiner

DIPIVEFRIN ORALLY DISINTEGRATING TABLET FORMULATIONS

CROSS REFERENCE TO RELATED APPLICATIONS

This application claims priority to U.S. Provisional Application No. 62/812,540 filed on Mar. 1, 2019, and all the benefits accruing therefrom under 35 U.S.C. § 119(b), the content of which is incorporated by reference in its entirety.

FIELD OF THE DISCLOSURE

This disclosure provides orally disintegrating dipivefrin tablet formulations. The disclosure also provides a method of treating a patient who has a condition responsive to epinephrine such as a cardiac event, asthma, croup, cancer, a microbial infection, Addison's disease, or an allergic reaction, particularly anaphylaxis by administering an orally disintegrating dipivefrin tablet formulations to the patient.

BACKGROUND

Dipivefrin is a dipivaloyl ester prodrug of epinephrine. Dipivefrin is 100-600 times more lipophilic than epinephrine, accordingly, eight to ten times more dipivefrin than epinephrine enters the rabbit eye. The ocular penetration of dipivefrin is 17 times greater than that of epinephrine in human eyes. Dipivefrin is hydrolyzed rapidly to epinephrine in the cornea and the anterior chamber. When instilled as a 0.5% solution in human eyes, 80% of the dipivefrin is converted into epinephrine within 30 minutes. Dipivefrin hydrochloride has been approved for ocular use as a 0.1% ophthalmic solution indicated as initial therapy for the control of intraocular pressure in chronic open-angle glaucoma.

Epinephrine is used to treat a number of conditions including anaphylaxis, cardiac arrest, and superficial bleeding, asthma and croup. Injectable epinephrine has also been shown to be efficacious for preventing and treating cancer. U.S. Pat. No. 5,925,682 discloses that injecting a mammal with an effective amount of epinephrine results in the significant reduction of tumorous growth. Epinephrine may also be efficacious in treating microbial infections. Epinephrine, delivered via intramuscular or subcutaneous injection, is a drug of choice for emergency treatment of anaphylaxis. It is commercially available in injectable form delivered by autoinjectors or pre-filled syringes. In the US, epinephrine injection comes in 0.5 milligrams (mg), 0.3 mg, 0.15 mg and 0.1 mg dosage strengths for emergency treatment of anaphylaxis. U.S. Pat. No. 10,039,710 B2 discloses epinephrine spray formulations for anaphylaxis that can be administered via the sublingual or intranasal route. There remains a need for effective, economical, and easy to use formulations that can quickly deliver epinephrine into a patient's bloodstream. The current disclosure provides an effective, convenient, an easy to use formulation capable of quickly delivering a therapeutic level of epinephrine to a patient's bloodstream and provides additional advantages.

SUMMARY

This disclosure is directed to a dipivefrin orally disintegrating tablet (ODT), comprising dipivefrin hydrochloride, a binder, a disintegrant and/or matrix former, and a taste masking agent. In certain embodiments the ODT comprises about 0.01 mg, to about 60 mg L-dipivefrin hydrochloride or 0.5 mg, 1.0 mg, 2.5 mg, or 5 mg L-dipivefrin hydrochloride. The dipivefrin ODT of the disclosure can have a total tablet weight of less than 100 mg. The dipivefrin ODT of the disclosure can comprise 10 to 70% binder weight percent (wt %), 5 to 50% matrix former and/or disintegrant (wt %), and 1 to 20% taste masking agent (wt. %). In certain embodiments the ODT of the disclosure can comprise 5 to 15% dipivefrin HCl, 25 to 40% matrix former, 35 to 50% binder, and 10 to 20% sweetener, where all percentages are weight percents. In certain embodiments the ODT of the disclosure can comprise 5 to 15% dipivefrin HCl, 25 to 35% matrix former, 35 to 45% binder, and 10 to 20% sweetener, where all percentages are weight percents. In certain embodiments the ODT of the disclosure can comprise 5 to 15% dipivefrin HCl, 20 to 40% matrix former, 19 to 73% binder, and 5 to 10% sweetener, where all percentages are weight percents. In certain embodiments the ODP comprises L-dipivefrin HCl, 0.4-51%, 9.94-53.05% gelatin (wt %), 20.98-39.75% glycine (wt %), 10.49-19.87% PVP K30 (wt %), 5.25-9.94% citric acid (wt %), and 5.25-9.94% saccharin sodium (wt %). In certain embodiments the ODP comprises L-dipivefrin HCl, 9-53% gelatin (wt %), 20-40% glycine (wt %), 10-20% PVP K30 (wt %), 5-10% citric acid (wt %), and 5-10% saccharin sodium (wt %).

The binder can comprise gelatin and/or povidone. The matrix former can be glycine or mannitol. The taste masking agent can include citric acid and/or a sweetener such as sucralose and sodium saccharin. The dipivefrin ODT composition can optionally contain a chelating agent. The dipivefrin ODT composition can optionally contain an antioxidant. The dipivefrin ODT composition can optionally contain a permeation enhancer. The dipivefrin ODT composition can optionally contain a flavoring agent. The dipivefrin ODT composition can optionally contain a colorant. The dipivefrin ODT composition of the present disclosure can optionally contain a pH modifier.

The dipivefrin ODT of this disclosure is suitable for treating conditions in a subject such as anaphylaxis in which epinephrine is urgently needed in the subject's systemic circulation. As such the disclosure include dipivefrin ODTs capable of providing an epinephrine $T_{max}$ of less than 60 min or in certain embodiments, less than 45 minutes from administration to the subject, and an epinephrine plasma $C_{max}$ of 0.1 to 50 nanogram per milliliter (ng/mL) when administered to a subject.

In certain embodiments the dipivefrin ODT contains not more than 10 mg of dipivefrin hydrochloride and provides a plasma level of epinephrine at 20 minutes after administration that is equal or greater than a plasma level of epinephrine provided by a US FDA-approved injectable epinephrine dosage form. The US FDA-approved injectable epinephrine dosage form can be a 0.5 mg, 0.3 mg, 0.15 mg, or 0.1 mg epinephrine dosage form for intramuscular administration. The US FDA-approved injectable epinephrine dosage form can be a 0.5 mg, 0.3 mg, 0.15 mg, or 0.1 mg epinephrine dosage form for subcutaneous administration.

The disclosure includes a method of treating a subject suffering from a condition responsive to epinephrine by administering a dipivefrin ODT of the disclosure. The condition responsive to epinephrine can be a breathing difficulty, such as a breathing difficulty is associated with anaphylaxis, asthma, bronchitis, emphysema, croup, or a respiratory infection. In certain embodiments the condition responsive to epinephrine is anaphylaxis.

The disclosure includes a method of reducing the severity of an allergic reaction or anaphylaxis or inhibiting the onset of an allergic reaction or anaphylaxis in a subject, comprising administering a dipivefrin ODT of the disclosure to the subject following exposure of the subject to an allergen. The dipivefrin ODT of the disclosure can be the only active agent administered to a subject or can be administered together with another active agent such as an antihistamine, for example diphenhydramine.

The disclosure includes a method for treating a condition responsive to epinephrine in a subject, in which the subject has a deficiency of epinephrine. The deficiency can be short term or chronic. Such conditions include Addison's disease, adrenal hyperplasia, hypoglycemia, or chronic active hepatitis.

DETAILED DESCRIPTION

Terminology

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "dipivefrin orally disintegrating tablet" or "dipivefrin orally dissolving tablet" or "dipivefrin ODT" refers to an orally disintegrating tablet comprising dipivefrin (freebase), or a pharmaceutically acceptable salt, solvate, or polymorph of dipivefrin. A preferred dipivefrin ODT comprises dipivefrin hydrochloride or L-dipivefrin hydrochloride.

The structures of dipivefrin and L-dipivefrin are as follows:

(dipivefrin)

(L-dipivefrin)

The IUPAC name of dipivefrin is 4-(1-hydroxy-2-(methylamino)ethyl)-1,2-phenylene bis(2,2-dimethylpropanoate). The synonyms of dipivefrin are [±]-3,4-Dihydroxy-α-[(methylamino)methyl]benzyl alcohol 3,4-dipivalate, 1-(3', 4'-Dipivaloyloxyphenyl)-2-methylamino-1-ethanol, 4-[1-Hydroxy-2-(methylamino)ethyl]-O-phenylene dipivalate, Dipivalyl Epinephrine, and [2-(2,2-Dimethylpropanoyloxy)-4-[1-hydroxy-2-(methylamino)ethyl]phenyl] 2,2-dimethylpropanoate. Dipivefrin has Chemical Abstract Service Registry Number (CAS Reg. No.) 52365-63-6, Dipivefrin hydrochloride has CAS Reg. No. 64019-93-8. L-dipivefrin has CAS Reg. No. 56298-24-9 and L-dipivefrin hydrochloride has CAS Reg. No. 79071-01-5.

As used herein, the term "pharmaceutically acceptable salt" is a salt formed from, for example, an acid and a basic group of a dipivefrin composition. Illustrative salts include, but are not limited to, sulfate, citrate, acetate, oxalate, chloride, acid chloride, bromide, iodide, nitrate, phosphate, acid phosphate, isonicotinate, lactate, salicylate, acid citrate, tartrate, oleate, tannate, pantothenate, bitartrate, ascorbate, succinate, maleate, besylate, gentisinante, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In an embodiment, the salt of dipivefrin is a hydrochloride salt. Unless clearly contraindicated by the context, "dipivefrin" includes the pharmaceutically acceptable salts of dipivefrin.

The term "pharmaceutically acceptable salt" also refers to a salt prepared from a composition having an acidic functional group, such as a carboxylic acid functional group, and a pharmaceutically acceptable inorganic or organic base and also to a salt prepared from a composition having a basic functional group, such as an amino functional group, and a pharmaceutically acceptable inorganic or organic acid.

An "active agent" means a compound (including for example, dipivefrin), element, or mixture that when administered to a subject, alone or in combination with another compound, element, or mixture, confers, directly or indirectly, a physiological effect on the subject. The indirect physiological effect may occur via a metabolite or other indirect mechanism.

The terms "administer", "administering", "administered" or "administration" refer to any manner of providing an active agent (such as dipivefrin or a pharmaceutically acceptable salt thereof) to a subject or patient. Routes of administration can be accomplished through any means known by those skilled in the art. Such means include oral, buccal, intravenous, subcutaneous, intramuscular, transdermal, and inhalation, sublingual, intranasal. Oral administration is a preferred route of dipivefrin administration.

The terms "taken orally" and "oral administration" refer to a manner of providing an active agent to a subject or patient by the mouth through the gastrointestinal tract (digestive tract, digestional tract, GI tract, GIT, gut, or alimentary canal) and are used interchangeably. The gastrointestinal tract is an organ system within humans and other animals which takes in food, digests it to extract and absorb energy and nutrients, and expels the remaining waste as feces. The mouth, esophagus, stomach and intestines are part of the gastrointestinal tract.

A "dosage form" means a unit of administration of an active agent. In this disclosure the dosage forms are orally disintegrating tablets.

An "orally disintegrating (or dissolving) tablet" is a solid dosage form that disintegrates or dissolves rapidly, usually within a matter of seconds, when placed in the mouth. Orally disintegrating dosage forms are designed to disintegrate or dissolve rapidly on contact with saliva, thus eliminating the need for chewing, swallowing, or taking the solid dosage with water. An orally disintegrating dosage can promote pregastric absorption of the active ingredients through buccal, sublingual, oropharyngeal and esophageal membranes. As a result, an orally dissolving dosage can provide faster onset of action and higher bioavailability than a conventional solid dosage form.

A "pharmaceutically acceptable excipient" means an excipient that is useful in preparing a pharmaceutical composition that is generally safe, non-toxic, and neither biologically nor otherwise undesirable, and includes an excipient that is acceptable for veterinary use as well as human pharmaceutical use. A "pharmaceutically acceptable excipient" as used in the present application includes both one and more than one such excipient.

A "subject" is a human or non-human mammal, such as a companion animal, e.g. cat or dog. A subject can be a human or non-human patient in need of medical treatment.

A "therapeutically effective amount" or "effective amount" is that amount of a pharmaceutical agent to achieve a pharmacological effect. The term "therapeutically effective amount" includes, for example, a prophylactically effective amount, that is an amount effective to significantly reduce the probability of occurrence of a disorder in a patient at risk for the disorder. An "effective amount" of dipivefrin is an amount needed to achieve a desired pharmacologic effect or therapeutic improvement without undue adverse side effects. The effective amount of dipivefrin will be selected by those skilled in the art depending on the particular patient and the type of conditions being treated. It is understood that "an effective amount" or "a therapeutically effective amount" can vary from patient to patient, due to variation in general condition of the subject, the condition being treated, the severity of the condition being treated, and the judgment of the prescribing physician. When discussing a method of treating cancerous tissue, an effective amount includes an amount effective to have a statistically significant and favorable effect on the rate of the patient's cancer proliferation over time or on a level of biological marker for the cancer.

The terms "treating" and "treatment" mean implementation of therapy with the intention of reducing in severity or frequency symptoms, elimination of symptoms or underlying cause, prevention of the occurrence of symptoms or their underlying cause, or the improvement or remediation of damage due to a disorder or disease. In certain embodiments "treatment" includes prophylactic treatment, which includes administering an amount of dipivefrin effective to significantly reduce the proliferation of cancerous tissue, reduce the chance of infection of a patient by a microbial pathogen. In certain embodiments treatment includes inhibiting the onset of anaphylaxis or reducing the severity of allergy symptoms in a subject exposed to an allergen.

Orally Disintegrating Tablets

An orally disintegrating tablet or orally dissolving tablet (ODT) is a drug dosage form available for a limited range of over-the-counter (OTC) and prescription medications. ODTs differ from traditional tablets in that they are designed to be dissolved on the tongue rather than swallowed whole. The ODT serves as an alternative dosage form for patients who experience dysphagia (difficulty in swallowing) or for patients for whom compliance is a known issue and need an easier to swallow dosage form to ensure that medication is taken. Dysphagia is common among all age groups. It is observed in about 20% of the general population, 33% of hospital patients, and in up to 40% of patients in long-term care facilities. ODT dosages forms are also an option for pediatric patients too young to swallow pills. ODTs also have a faster onset of action than tablets or capsules due to pregastric absorption (absorption from the mouth, pharynx and esophagus as the saliva passes down into the stomach), and can be conveniently taken without water.

There has been well documented significant underutilization of epinephrine autoinjectors in the anaphylactic community due to patients' fear of injection, the inconvenience of carrying epinephrine autoinjectors, which must be maintained at a temperature between 20 and 25° C., and the high cost of epinephrine autoinjectors. ODTs are particularly suitable for delivering epinephrine for emergency treatment of anaphylaxis given their unique advantages as patient-friendly and convenient pharmaceutical dosage forms that can be taken anytime, anywhere and by anyone without water and the need to swallow a whole tablet. It is well known in the art that epinephrine is not absorbed when taken orally, precluding the development of epinephrine ODTs for anaphylaxis. The inventor has developed new orally disintegrating dipivefrin tablets, suitable for commercial use. The ODTs of this disclosure are stable at temperatures of from less than 0° C. to at least 60° C. and thus provide a significant advantage over epinephrine auto-injectors because they do not need to be stored within a narrow temperature range. Stability of the dipivefrin ODTs of this disclosure can be further enhanced by excluding moisture and oxygen during their manufacture and storage.

The dipivefrin ODTs of this disclosure contain from about 0.01 to about 60 mg dipivefrin or a dipivefrin salt such as dipivefrin hydrochloride. This disclosure includes ODTs containing 0.1 mg, 0.5 mg, 1.0 mg, 2.0 mg, 3.0 mg, 4.0 mg, 5.0 mg, 7.0 mg. 7.5 mg, 10 mg, 12 mg, 15 mg, or 20 mg dipivefrin HCl.

The dipivefrin ODTs of this disclosure may contain a binder. Non-limiting examples of suitable binders include water-soluble, alcohol-soluble or acetone/water soluble binders, e.g. gelatin, dextran, alginates, gum Arabic, modified starch, polyvinylpyrrolidone (PVP, also called povidone, plasdone, polyvidone) including PVP K30 (Cas. Reg. No. 9003-39-8, the K number refers to the mean molecular weight of the povidone, PVP K30 has an average molecular weight of 40,000), corn starch, polyethylene oxide, polyethylene glycol, hydroxypropyl methylcellulose (HPMC), methylcellulose, and hydroxypropylcellulose (HPC) and combinations thereof. The amount of binder in the dipivefrin ODT ranges from 10% to 70% (wt %), including 20% to 70%, 25% to 65%, 30% to 60%, 35% to 60%, 40% to 60%, 45% to 60% and 30% to 35% (wt %).

The dipivefrin ODTs of this disclosure optionally contain a disintegrant. When the ODTs are prepared by direct compression a disintegrant is typically present. The disintegrant may be any disintegrant suitable for orally disintegrating tablets, for example the disintegrant may be a sugar alcohol such as sorbitol, mannitol, xylitol, isomalt, and hydrogenated starch hydrolysates, or an amino acid such as glycine, the disintegrant may also be crospovidone (cross-linked PVP), sodium starch glycolate, crosslinked sodium carboxymethyl cellulose, low substituted hydroxypropylcellulose, or a mixture of any of the foregoing. In certain embodiments the disintegrant is mannitol, glycine, or a combination thereof. The amount of disintegrant in the ODTs can be from 1% to 50% (wt %), 10% to 50%, 15% to 50%, 20% to 50%, 20% to 40%, 25% to 40%, or 30% to 40% (wt %).

The dipivefrin ODTs of this disclosure optionally contain a matrix former. Dipivefrin ODTs of this disclosure prepared by lyophilization contain a matrix former and optionally contain a disintegrant. The matrix former is preferably a crystalline material that remains crystalline upon lyophilization but dissolves readily in saliva. Matrix formers include glycine, crystalline sugars such as mannitol (including D-mannitol), erythritol, and xylitol, microcrystalline cellulose, maltodextran, and crystalline cellulose.

The dipivefrin ODTs of this disclosure may include a taste masking agent. Suitable taste masking agents include, but are not limited to, artificial and natural flavorants, citric acid, and sweeteners, including artificial sweeteners, nutritive sweeteners, and sugar alcohols. Examples of sweeteners useful as taste masking agents include saccharin, aspartame, acesulfame K, neotame, sodium saccharin, sucralose, trehalose, tagatose, mannitol, sorbitol, xylitol, erythritol, maltitol, sucrose, fructose, and glucose. Suitable flavorants include, but are not limited to, peppermint oil, menthol, spearmint oil, citrus oil, cinnamon oil, strawberry flavor, cherry flavor, raspberry flavor, orange oil, and combinations of any of the foregoing.

The amount of taste-masking agent in the dipivefrin ODTs of this disclosure can be from 0.1% to 25% (wt %), 0.5% to 25%, 1% to 25%, 2% to 25%, 5% to 25%, 10% to 25%, 1% to 20%, 2% to 20%, 5% to 20%, 10% to 20%, 0.5% to 10%, 1% to 10%, or 5% to 10% (wt %). In certain embodiments the taste masking agent is citric acid, sucralose, or saccharin, or a combination thereof.

The dipivefrin ODT composition can optionally contain a chelating agent. Suitable chelating agents for the dipivefrin ODTs of this disclosure include, but are not limited to, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans diaminocyclohexanetetraacetic acid (DCTA), diethylenetriaminepentaacetic acid, bis(aminoethyl)glycolether-N,N,N',N'-tetraacetic acid, iminodiacetic acid, citric acid, tartaric acid, fumaric acid, or a salt thereof. The amount of chelating agent in the dipivefrin ODTs of this disclosure can be from 0.1% to 25% (wt %), 0.5% to 25%, 1% to 25%, 2% to 25%, 5% to 25%, 10% to 25%, 1% to 20%, 2% to 20%, 5% to 20%, 10% to 20%, 0.5% to 10%, 1% to 10%, or 5% to 10% (wt %).

The dipivefrin ODT composition can optionally contain an antioxidant. Antioxidants suitable for the dipivefrin ODTs of the present disclosure include, but are not limited to, butylated hydroxyanisole (BHA), butylated hydroxytoluene (BHT), ascorbic acid, methionine, sodium ascorbate, sodium thiosulfate, sodium bisulfite, sodium metabisulfite, ascorbyl palmitate, thioglycerol, alpha tocopherol (vitamin E), cysteine hydrochloride and combinations thereof.

The dipivefrin ODT composition of the present disclosure can optionally contain a permeation enhancer. Permeation enhancers suitable for the present disclosure include, but are not limited to, caprylic acid, oleic acid, polysorbate 80 (Polyethlene glycol sorbitan monooleate, CAS Reg. No. 9005-65-6), menthol, EDTA, sodium edetate, cetylpyridinium chloride, sodium lauryl sulfate, citric acid, sodium desoxycholate, sodium deoxyglycolate, glyceryl oleate, L-lysine, and combinations thereof.

The dipivefrin ODT composition of the present disclosure can optionally contain a pH modifier. pH modifiers suitable for the present invention include, but are not limited to, hydrochloric acid, citric acid, fumaric acid, lactic acid, sodium hydroxide, mono or dibasic sodium phosphate, amino acids, sodium citrate, sodium bicarbonate, sodium carbonate, ammonium carbonate and a combinations of any of the foregoing. Typically, when dissolved in deionized water, the dipivefrin ODT composition of this disclosure has a pH of from 1-7, in some embodiments a pH of from 1-5, and in some embodiments a pH of from 2.5-3.5.

The dipivefrin ODTs can optionally contain a pharmaceutically acceptable colorant. The dipivefrin ODTs of this disclosure can optionally contain a coating, such as an immediate release coating.

In certain embodiments, the dipivefrin ODTs may be freeze dried tablets which may contain a binder, optionally a disintegrant, at least one matrix forming agent, also known as matrix former, and at least one taste masking agent. The taste masking agent may include a sweetener. Typical packaging of the freeze-dried dipivefrin ODTs may include aluminum blister packs. The blister pack comprises a multi-layered (e.g. 5 layers) laminated blister film and a lidding foil. The lidding foil is peelable such that the lidding foil over each tablet may be removed to reach the tablet.

The dipivefrin ODTs can be manufactured by any of the manufacturing processes known in the art for preparing ODTs. For example, the dipivefrin ODTs of this disclosure can be manufactured using conventional tableting process such as direct compression. The dipivefrin ODTs can also be manufactured by wet granulation followed by drying the granules and compressing the granules into tablets. The dipivefrin ODTs of the disclosure can be manufactured by a tablet molding process using water soluble excipients such as saccharides. Direct compression tablets of this disclosure typically contain a disintegrant.

In certain embodiments the total weight of the ODT is less than 100 mg, less than 70 mg, less than 50 mg, less than 40 mg, less than 30 mg, less than 20 mg, or less than 10 mg.

In certain embodiments the dipivefrin orally disintegrating tablet dissolves completely in simulated saliva at 37° C. in less than 30 seconds, or less than 10 seconds or in less than 5 seconds.

In certain embodiments the dipivefrin orally disintegrating tablet dissolves completely in water at ambient temperature in less than 30 seconds, or less than 10 seconds or in less than 5 seconds.

Methods of Treatment

Orally administered dipivefrin is well absorbed and hydrolyzed rapidly in the blood to deliver epinephrine to the systemic circulation, thus could be useful in treating conditions responsive to epinephrine. The disclosure includes methods of treating a subject for a condition responsive to epinephrine by administering a dipivefrin ODT of this disclosure to the subject.

Conditions responsive to epinephrine includes breathing difficulty, including breathing difficulties associated with anaphylaxis, asthma, bronchitis, emphysema, croup, or a respiratory infection.

Conditions responsive to epinephrine also include allergic attack, severe allergic symptoms, and anaphylaxis. Methods of treatment include administering a dipivefrin ODT of this disclosure to a subject suffering from an allergic attack, severe allergies, or anaphylaxis. Methods of treatment of this disclosure also include administering a dipivefrin ODT of this disclosure to a subject after the subject has been exposed to a known allergen, and thereby decreasing the risk of an allergic attack, severe allergies, or anaphylaxis or lessening the severity of from an allergic attack, severe allergies, or anaphylaxis. The dipivefrin ODT can be administered as the only active agent or can optionally be administered together with another active agent such as an antihistamine or steroid. Examples of antihistamines include diphenhydramine, brompheniramine, cetirizine, chlorpheniramine, clemastine, fexofenadine, and loratidine.

Method of treatment includes administering a dipivefrin ODT of the disclosure to a subject having insufficient epinephrine. Such a condition can be a chronic condition or an acute condition. Examples include Addison's disease, adrenal hyperplasia, hypoglycemia, and chronic active hepatitis.

The condition responsive to epinephrine can be a cancer. The cancer can be skin cancer, brain cancer, a glioma, a sarcoma, breast cancer, lung cancer, non-small-cell lung cancer, mesothelioma, appendicular cancer, a genitourinary cancer, a renal cell carcinoma, prostate cancer, bladder cancer, testicular cancer, penile cancer, cervical cancer, ovarian cancer, von Hippel Lindau disease, a head and neck cancer, a gastrointestinal cancer, a hepatocellular carcinoma, gallbladder cancer, esophageal cancer, gastric cancer, colorectal cancer, pancreatic cancer, a neuroendocrine tumor, a thyroid tumor, a pituitary tumor, an adrenal tumor, a hematological malignancy, a lymphoma, a leukemia, or a combination thereof. The condition can be skin cancer, and the skin cancer is a melanoma. Dipivefrin or its pharmaceutically acceptable salt can be an adjunctive anticancer treatment and the method comprises administering at least one additional anticancer treatment to the subject.

The condition responsive to epinephrine can be a microbial infection. The microbial infection can be a bacterial, viral, fungal, or parasitic infection. The microbial infection can be a viral infection, such as an influenza infection. The microbial infection can be a bacterial infection, such as a methicillin-resistant *Staphylococcus aureus* (MRSA) infection. Dipivefrin or its pharmaceutically acceptable salt can be an adjunctive antimicrobial agent and the method further comprises the use of at least one additional antimicrobial agent for treating infection in the subject. The additional antimicrobial agent can be an antibiotic. The additional antimicrobial agent can be an antiviral agent.

The condition responsive to epinephrine can be an autoimmune disorder. The autoimmune disorder can be rheumatoid arthritis, systemic lupus erythematosus (lupus), multiple sclerosis (MS), Type 1 diabetes mellitus, Guillain-Barre syndrome, chronic inflammatory demyelinating polyneuropathy, psoriasis, Graves' disease, Hashimoto's thyroiditis, Myasthenia gravis, vasculitis, and inflammatory bowel disease (IBD). Ulcerative colitis and Crohn's disease are the two major forms of IBD. Dipivefrin or its pharmaceutically acceptable salt can be an adjunctive agent and the method further comprises the use of at least one additional active agent for treating an autoimmune disease in the subject. The additional active agent can include a steroid, immune-suppressing medicines, pyridostigmine, insulin or synthetic thyroid hormone.

Examples of the conditions responsive to epinephrine include croup, superficial bleeding, cardiac arrests, and hypotension.

EXAMPLES

General Methods

Simulated Saliva Composition

TABLE A

Table A provides the composition of simulated saliva used for in vitro evaluation dipivefrin ODTs. 1 normal (N) HCl is used to adjust simulated saliva pH to 6.8.
Composition of simulated saliva

| Ingredient | Amount |
| --- | --- |
| NaCl | 4.0 g |
| $KH_2PO_4$ | 0.095 g |
| $Na_2HPO_4 \cdot 7H_2O$ | 2.245 g |
| Deionized water | q.s. to 500 mL | q.s.: quantum sufficit

In Vitro Dissolution Testing Method

An appropriate volume of simulated saliva needed to obtain a 1 mg/ml dipivefrin HCl concentration after dissolution is accurately weighed, placed in a glass vial and heated at 37° C. One dipivefrin HCl ODT is dropped into the solution and gently swirled until the tablet is completely dissolved. The dissolution time is recorded.

HPLC Analysis of Dipivefrin HCl ODT

HPLC (High-performance liquid chromatography) sample preparation: For dipivefrin HCl ODT 5.0 mg (refers to the weight of dipivefrin HCl salt), 5.00 gram (g) of the simulated saliva was accurately weighed into a 20 milliliters (mL) glass scintillation vial. For dipivefrin HCl ODT 2.5 mg, 2.50 g of simulated saliva was used. The vials were placed in an oil bath set at 37° C. for 5 min. One tablet was placed in the appropriate vial which was gently swirled by hand until complete dissolution is achieved. The dissolution time was recorded. The dissolution samples were immediately analyzed by HPLC for purity and assay.

HPLC Method:
Column: Phenomenex Gemini C18, 100×4.6 millimeter (mm), 3.0 micrometer (μm)
Flow rate: 1.0 mL/min
Detection: 254 nanometer (nm)
Temperature: 30° C.
Injection volume: 10 microliter (μL)
Mobile phase: A: 0.1% Trifluoroacetic acid (TFA) in water
B: 0.1% TFA in acetonitrile
Gradient:

| Time (min) | Solvent A (%) | Solvent B (%) |
|---|---|---|
| 0 | 90 | 10 |
| 4 | 50 | 50 |
| 6 | 35 | 65 |
| 8 | 90 | 10 |
| 12 | 90 | 10 |

Example 1. Preparation of Dipivefrin HCl ODTs

The preparation of dipivefrin HCl ODTs of various strengths is disclosed in this example. The strengths of the tablets in this patent application refer to the weight of the dipivefrin HCl salt contained in each tablet unless specified otherwise. Diluent solution (pre-lyophilization (lyo) solution minus dipivefrin HCl) is prepared according to Table 1.1. To make a dipivefrin HCl ODT of a desired strength, the desired amount of dipivefrin HCl is dissolved in an appropriate amount of the diluent to obtain the dipivefrin HCl lyo solution. An aliquot of the lyo solution is then dispensed into blister pack pockets. The filled blister pack was then frozen on dry ice for at least one hour and freeze dried to obtain the dipivefrin HCl ODTs.

TABLE 1.1

Composition of Diluent Solution

| Ingredient | Function | % wt/wt. of water | Batch size (g) |
|---|---|---|---|
| Gelatin | Binding agent | 2 | 0.4 |
| D-Mannitol | Matrix former/ disintegration enhancing agent | 1 | 0.2 |
| Glycine | Matrix former | 1 | 0.2 |
| PVP K30 | Binding agent | 1 | 0.2 |
| Citric acid | Taste masking agent | 0.5 | 0.1 |
| Sodium saccharin | Sweetener | 0.5 | 0.1 |
| Deionized water | Solvent | | 20.0 |
| Total | | | 21.2 |

To prepare the diluent, gelatin is first dissolved in deionized water at about 40° C. to obtain a clear solution. The remaining excipients listed in Table 1.1 are then added and dissolved under stirring to obtain the diluent solution with pH 3.43.

Dipivefrin HCl ODT 0.5 mg

Dipivefrin HCl (5 mg) was dissolved in 5.30 g of the diluent solution to obtain a lyo solution. The lyo solution (535 μL) was then dispensed into each pocket of a blister pack with a diameter of 13 mm and a depth of 3 mm resulting in a dose of 0.5 mg per tablet. The tablet blister pack was then placed on top of dry ice for one hour. The frozen tablets were freeze dried for 24 hour (h) using a VirTis Sentry 2.0 (SP Scientific) Freeze Dryer with a condenser temperature of −90° C. and a pressure of 50 millitorr (mTorr). The lyophilized tablets were white, smooth, elegant and had sufficient strength for manual handling. Tablet weight: 29.87 mg±0.29 mg (SD, N=9). In vitro dissolution in simulated saliva at 37° C.: 2.30 seconds; In vivo dissolution time: 5.03 seconds; Dipivefrin HCl assay by HPLC: 96.3%.

Dipivefrin HCl ODT 1.0 mg

Dipivefrin HCl (10 mg) was dissolved in 4.46 g of the diluent solution to obtain a lyo solution. The lyo solution (446 μL) was then dispensed into each pocket of a blister pack with a diameter of 13 mm and a depth of 3 mm resulting in a dose of 1.0 mg per tablet. The tablet blister pack was then placed on top of dry ice for one hour. The frozen tablets were freeze dried for 24 h using a VirTis Sentry 2.0 (SP Scientific) Freeze Dryer with a condenser temperature of −90° C. and a pressure of 50 mTorr. The lyophilized tablets were white, smooth, elegant and had sufficient strength for manual handling. Tablet weight: 25.02 mg±0.33 mg (SD, N=10). In vitro dissolution in simulated saliva at 37° C.: 3.82 seconds; Dipivefrin HCl assay by HPLC: 98.1%.

Dipivefrin HCl ODT 2.5 mg

Dipivefrin HCl (25 mg) was dissolved in 5.30 g of the diluent solution to obtain a lyo solution. The lyo solution (535 μL) was then dispensed into each pocket of a blister pack with a diameter of 13 mm and a depth of 3 mm resulting in a dose of 2.5 mg per tablet. The tablet blister pack was then placed on top of dry ice for one hour. The frozen tablets were freeze dried for 24 h using a VirTis Sentry 2.0 (SP Scientific) Freeze Dryer with a condenser temperature of −90° C. and a pressure of 50 mTorr. The lyophilized tablets were white, smooth, elegant and had sufficient strength for manual handling. Tablet weight: 32.04 mg±0.42 mg (SD, N=9). In vitro dissolution in simulated saliva at 37° C.: 3.66 seconds; In vivo dissolution time: 3.86 seconds; Dipivefrin HCl assay by HPLC: 98.8%.

Dipivefrin HCl ODT 5.0 mg

Dipivefrin HCl (50 mg) was dissolved in 5.30 g of the diluent solution to obtain a lyo solution. The lyo solution (535 μL) was then dispensed into each pocket of a blister pack with a diameter of 13 mm and a depth of 3 mm resulting in a dose of 2.5 mg per tablet. The tablet blister pack was then placed on top of dry ice for one hour. The frozen tablets were freeze dried for 24 h using a VirTis Sentry 2.0 (SP Scientific) Freeze Dryer with a condenser temperature of −90° C. and a pressure of 50 mTorr. The lyophilized tablets were white, smooth, elegant and had sufficient strength for manual handling. Tablet weight: 34.48 mg±0.51 mg (SD, N=9). In vitro dissolution in simulated saliva at 37° C.: 4.03 seconds. Dipivefrin HCl assay by HPLC: 96.7%.

Example 2. Comparison of Dipivefrin HCl ODTs Containing Sodium Saccharin and Sucralose as Sweeteners The effect of sweetener on the drying (final tablet weight) of dipivefrin HCl ODTs is illustrated by this example. The diluent compositions are listed in Table 2.1.

TABLE 2.1

Diluent Compositions

| Ingredient | % wt/wt of water | Sodium saccharin containing diluent (SS-diluent) Batch size (g) | Sucralose containing diluent (SU-diluent) Batch size (g) |
|---|---|---|---|
| Gelatin | 2 | 0.4 | 0.4 |
| D-mannitol | 1 | 0.2 | 0.2 |
| Glycine | 1 | 0.2 | 0.2 |
| PVP k30 | 1 | 0.2 | 0.2 |
| Citric acid | 0.5 | 0.1 | 0.1 |
| Sodium saccharin | 0.5 | 0.1 | — |
| Sucralose | 0.5 | — | 0.1 |
| Deionized water | 20 | 20 | |
| 1N HCl for pH adjustment | | pH 3.0 | pH 3.0 |

The 2.5 mg and 5.0 mg dipivefrin HCl ODT tablets using the sodium saccharin containing diluent (SS-diluent) and sucralose containing diluent (SU-diluent) were prepared at the same time in the same fashion as described in the Example 1. The tablets were removed from the blister packs, individually weighed and stored in closed glass vials. One tablet from each group was tested for dissolution in simulated saliva at 37° C. at nominal drug concentration of 1.0 milligram per milliliter (mg/ml). The clear solutions from the dissolution tests were analyzed by HPLC for purity assessment and dipivefrin HCl assay. The results are summarized in Table 2.2, below. The sucralose containing dipivefrin HCl ODTs were observed to have significantly higher weights than those containing sodium saccharin at the same dipivefrin strength (p<0.05 for the 5 mg strength, p<0.01 for the 2.5 mg strength, two-tailed T-test). These results suggest that the dipivefrin HCl lyo solution containing sodium saccharin dried more efficiently than that containing sucralose as the sweetener.

TABLE 2.2

Comparison of dipivefrin HCl ODTs containing saccharin Sodium and sucralose

| Sweetener | Sodium Saccharin | | Sucralose | |
|---|---|---|---|---|
| Tablet strength | 2.5 mg | 5.0 mg | 2.5 mg | 5.0 mg |
| Average tablet weight (mg ± standard deviation (SD), N = 12) | 31.08 ± 0.60 | 34.11 ± 0.67 | 33.14 ± 1.50 | 34.82 ± 0.85 |
| Assay (% Label Claim (LC)) | 93.6 | 100.7 | 101.1 | 103.0 |
| In vitro dissolution in simulated saliva (s) | 2.92 | 4.57 | 1.56 | 7.30 |

The 5 mg tablets containing sodium saccharin and sucralose were removed from the blister packs and assessed in side by side stability studies at 60° C. in closed glass vials. Stability data are summarized in Tables 2.3 and 2.4. The main degradants are a pair of monopivaloylepinephrine isomers as shown by liquid chromatography-mass spectrometry (LCMS), formed by partial ester hydrolysis of dipivefrin. Consistent with their higher tablet weight, the sucralose containing dipivefrin HCl ODTs appeared to suffer from more hydrolytic degradation at 60° C. after 5 weeks.

TABLE 2.3

Dipivefrin HCl ODT 5 mg containing sodium saccharin, stored in closed glass vials at 60° C.

| Time point | | Initial | 1 week | 5 week |
|---|---|---|---|---|
| Tablet appearance | | white | white | White |
| In vitro dissolution time (seconds) | | 4.57 | 2.64 | 3.27 |
| HPLC (assay % of dipivefrin HCl) | | 100.7 | 94.0 | 90.7 |
| HPLC (area %) | Relative Retention Time (RRT) | | | |
| Dipivefrin | 1.000 | 99.63 | 97.21 | 1.70 |
| 3- or 4-monopivaloyle-pinephrine | 0.701 | 0.09 | 0.83 | 2.71 |
| 4- or 3-monopivaloyle-pinephrine | 0.773 | 0.28 | 1.03 | 94.34 |
| 4-[(methylamino)acetyl]-1,2-phenylenedipivalate | 1.036 | ND | 0.92 | 1.24 |

TABLE 2.4

Dipivefrin HCl ODT 5 mg containing sucralose, stored in closed glass vials at 60° C.

| Time point | | Initial | 1 week | 5 week |
|---|---|---|---|---|
| Tablet appearance | | white | White | White |
| In vitro dissolution time (seconds) | | 7.30 | 2.76 | 1.55 |
| HPLC (assay % of dipivefrin HCl) | | 103.0 | 101.0 | 93.8 |
| HPLC (area %) | Relative Retention Time (RRT) | | | |
| Dipivefrin | 1.000 | 99.67 | 97.62 | 91.63 |
| 3- or 4-monopivaloyle-pinephrine | 0.701 | 0.11 | 0.85 | 2.56 |
| 4- or 3-monopivaloyle-pinephrine | 0.773 | 0.22 | 1.02 | 4.72 |
| 4-[(methyl amino)acetyl]-1,2-phenylene dipivalate | 1.036 | ND | 0.5 | 1.09 |

Example 3. Preparation of Dipivefrin HCl ODT Formulations Free of D-Mannitol and Stability This example reports the preparation of dipivefrin HCl ODTs that do not contain D-mannitol as the matrix forming agent and their in vitro dissolution property and stability. The diluent composition is shown in Table 3.1 below which gives a clear solution with a pH 2.99.

TABLE 3.1

Diluent composition free of D-mannitol

| Ingredient | % wt/wt of water | Batch size (g) |
|---|---|---|
| Gelatin | 2.11 | 0.300 |
| Glycine | 2.11 | 0.300 |
| PVP K30 | 1.05 | 0.150 |
| Citric acid | 0.53 | 0.075 |
| Sodium saccharin | 0.53 | 0.075 |
| 1N HCl | 5.26 | 0.750 |
| Deionized water | | 14.250 |
| Total | | 15.900 |

Dipivefrin HCl ODT 5.0 mg

Dipivefrin HCl (60.24 mg) was dissolved in 6.36 g of the diluent solution to obtain the lyo solution. The lyo solution (535 μl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 h using a VirTis Sentry 2.0 (SP Scientific) Freeze Dryer with a condenser temperature of −90° C. and a pressure of 50 mTorr. The lyophilized tablets were white, smooth, and elegant and had sufficient strength for manual handling. Tablet weight: 35.92 mg±0.59 mg (SD, N=11). In vitro dissolution in simulated saliva at 37° C.: 2.55 seconds. Dipivefrin HCl assay by HPLC: 102.1%.

Dipivefrin HCl ODT 2.5 mg

Dipivefrin HCl (30.00 mg) was dissolved in 6.36 g of the diluent solution to obtain the lyo solution. The lyo solution (535 µl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 h using a VirTis Sentry 2.0 (SP Scientific) Freeze Dryer with a condenser temperature of −90° C. and a pressure of 50 mTorr. The lyophilized tablets were white, smooth, and elegant and had sufficient strength for manual handling. Tablet weight: 33.73 mg±0.48 mg (SD, N=11). In vitro dissolution in simulated saliva at 37° C.: 1.92 seconds. Dipivefrin HCl assay by HPLC: 102.1%.

Dipivefrin HCl ODT 1.0 mg

Dipivefrin HCl (13.20 mg) was dissolved in 7.00 g of the diluent solution to obtain the lyo solution. The lyo solution (535 µl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 h using a VirTis Sentry 2.0 (SP Scientific) Freeze Dryer with a condenser temperature of −90° C. and a pressure of 50 mTorr. The lyophilized tablets were white, smooth, and elegant and had sufficient strength for manual handling. Tablet weight: 31.30 mg±0.62 mg (SD, N=11). In vitro dissolution in simulated saliva at 37° C.: 2.28 seconds. Dipivefrin HCl assay by HPLC: 100.1%.

Dipivefrin HCl ODT 0.5 mg

Dipivefrin HCl (6.60 mg) was dissolved in 7.00 g of the diluent solution to obtain the lyo solution. The lyo solution (535 µl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 h using a VirTis Sentry 2.0 (SP Scientific) Freeze Dryer with a condenser temperature of −90° C. and a pressure of 50 mTorr. The lyophilized tablets were white, smooth, elegant and had sufficient strength for manual handling. Tablet weight: 32.24 mg±0.95 mg (SD, N=11). In vitro dissolution in simulated saliva at 37° C.: 2.02 seconds. Dipivefrin HCl assay by HPLC: 99.6%.

Both the 5 mg and 2.5 mg tablets were removed from the blister packs and put on stability at 60° C. in closed glass vials. The 2 week stability data at 60° C. are summarized in Tables 3.2 and 3.3.

TABLE 3.2

Stability of dipivefrin HCl ODT 5 mg mannitol free, stored in closed glass vials at 60° C.

| Time point | | Initial | 1 week | 2 week |
|---|---|---|---|---|
| Tablet appearance | | white | White | White |
| In vitro dissolution time (seconds) | | 2.55 | 2.58 | 1.37 |
| HPLC (assay % of Dipivefrin HCl) | | 102.1 | 98.5 | 96.0 |
| HPLC (area %) | Relative Retention Time (RRT) | | | |
| Dipivefrin | 1.000 | 99.82 | 97.49 | 97.42 |
| 3- or 4-monopivaloyle-pinephrine | 0.701 | 0.07 | 0.46 | 0.58 |
| 4- or 3-monopivaloyle-pinephrine | 0.773 | 0.11 | 0.69 | 0.59 |
| 4-[(methylamino)acetyl]-1,2-phenylene dipivalate | 1.036 | ND | 1.36 | 1.41 |

TABLE 3.3

Stability of dipivefrin HCl ODT 2.5 mg mannitol free, stored in closed glass vials at 60° C.

| Time point | | Initial | 1 week | 2 week |
|---|---|---|---|---|
| Tablet appearance | | white | White | White |
| In vitro dissolution time (seconds) | | 1.92 | 2.20 | 1.91 |
| HPLC (assay % of dipivefrin HCl) | | 102.1 | 99.2 | 94.5 |
| HPLC (area %) | Relative Retention Time (RRT) | | | |
| Dipivefrin | 1.000 | 99.83 | 98.49 | 98.22 |
| 3- or 4-monopivaloylepinephrine | 0.701 | 0.05 | 0.23 | 0.21 |
| 4- or 3-monopivaloylepinephrine | 0.773 | 0.13 | 0.25 | 0.32 |
| 4-[(methylamino)acetyl]-1,2-phenylene dipivalate | 1.036 | ND | 1.03 | 1.26 |

Example 4. Preparation and Stability Testing of Dipivefrin HCl ODT Formulations Containing EDTA The diluent composition is shown in Table 4.1 below which gives a clear solution with pH 3.02.

TABLE 4.1

| Diluent composition | | |
|---|---|---|
| Ingredient | % wt/wt. of water | Batch size (g) |
| Gelatin | 2.00 | 0.300 |
| Glycine | 2.00 | 0.300 |
| EDTA sodium | 0.04 | 0.005 |
| Citric acid | 0.50 | 0.075 |
| Sodium saccharin | 0.50 | 0.075 |
| 1N HCl | 4.67 | 0.700 |
| Deionized water | | 15.000 |
| Total | | 16.455 |
| pH 3.02 | | |

Dipivefrin HCl ODT 5.0 mg

Dipivefrin HCl (66.4 mg) was dissolved in 7.00 g of the diluent solution to obtain the lyo solution. The lyo solution (535 µl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 hour (hr) at ambient and 60° C. for 20 hr using a VirTis Sentry 2.0 (SP Scientific) Freeze Dryer with a condenser temperature of −90° C. and a pressure of 50 mTorr. The lyophilized tablets were white, smooth, and elegant and had sufficient strength for manual handling. The tablets were removed from the blister packs, weighed individually and stored in a closed glass vial. Tablet weight: 28.76 mg±0.42 mg (SD, N=9). In vitro dissolution in simulated saliva at 37° C.: 1.56 seconds. Dipivefrin HCl assay by HPLC: 100.1%.

Dipivefrin HCl ODT 2.5 mg

Dipivefrin HCl (33.0 mg) was dissolved in 7.00 g of the diluent solution to obtain the lyo solution. The lyo solution (535 µl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 hr at ambient and 60° C. for 20 hr using a VirTis Sentry 2.0 (SP Scientific) Freeze Dryer with a condenser temperature of −90° C. and a pressure of 50 mTorr. The lyophilized tablets were white, smooth, and elegant and had sufficient strength for manual handling. The tablets were removed from the blister packs, weighed individually and stored in a closed glass vial. Tablet weight: 24.23 mg±0.53 mg (SD, N=9). In vitro dissolution in simulated saliva at 37° C.: 1.52 seconds. Dipivefrin HCl assay by HPLC: 93.0%.

The tablets were removed from the blister packs and assessed for stability at 60° C. in closed glass vials. The stability data are summarized in Tables 4.2 and 4.3.

TABLE 4.2

Stability of dipivefrin HCl ODT 5.0 mg containing EDTA, stored in closed glass vials at 60 ° C.

| Time point | | Initial | 1 week | 8 weeks |
| --- | --- | --- | --- | --- |
| Tablet appearance | | white | white | Slightly yellow |
| In vitro dissolution time (seconds) | | 1.56 | 1.51 | 3.00 |
| HPLC (assay % of dipivefrin HCl) | | 100.1 | 96.3 | 89.2 |
| HPLC (area %) | Relative Retention Time (RRT) | | | |
| Dipivefrin | 1.000 | 99.66 | 98.65 | 82.53 |
| 3- or 4-monopivaloylepinephrine | 0.701 | 0.11 | 0.48 | 1.94 |
| 4- or 3-monopivaloylepinephrine | 0.773 | 0.21 | 0.68 | 1.26 |
| 4-[(methylamino)acetyl]-1,2-phenylene dipivalate | 1.036 | 0.02 | 0.19 | 0.39 |
| Unknown impurity | 0.369 | ND | ND | 4.95 |
| Unknown impurity | 0.449 | ND | ND | 2.84 |
| Unknown impurity | 0.501 | ND | ND | 6.10 |

TABLE 4.3

Stability of dipivefrin HCl ODT 2.5 mg containing EDTA, stored in closed glass vials at 60 ° C.

| Time point | | Initial | 1 week | 8 week |
| --- | --- | --- | --- | --- |
| Tablet appearance | | white | White | Slightly yellow |
| In vitro dissolution time (seconds) | | 1.52 | 2.05 | 2.31 |
| HPLC (assay % of dipivefrin HCl) | | 93.0 | 94.5 | 85.8 |
| HPLC (area %) | Relative Retention Time (RRT) | | | |
| Dipivefrin | 1.000 | 99.66 | 99.01 | 85.91 |
| 3- or 4-monopivaloylepinephrine | 0.701 | 0.08 | 0.17 | 1.29 |
| 4- or 3-monopivaloylepinephrine | 0.773 | 0.22 | 0.46 | 1.11 |
| 4-[(methylamino)acetyl]-1,2-phenylene dipivalate | 1.036 | 0.04 | 0.36 | 0.83 |
| Unknown impurity | 0.369 | ND | ND | 1.81 |
| Unknown impurity | 0.449 | ND | ND | 3.44 |
| Unknown impurity | 0.501 | ND | ND | 4.33 |

Example 5. Dipivefrin HCl ODT Formulations Stored in Blister Packs with Silica Gel Packet This example demonstrates that keeping the dipivefrin HCl ODT tablets from moisture during preparation, packaging and handling is critical for their long term stability. The diluent composition was the same as that shown in Table 3.1 of Example 3.

Dipivefrin HCl ODT 5.0 mg

Dipivefrin HCl (66.4 mg) was dissolved in 7.00 g of the diluent solution to obtain the lyo solution. The lyo solution (535 µl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 hr at ambient temperature. One tablet was removed from the blister pack and tested for in vitro dissolution, HPLC purity and HPLC assay (T0). The blister pack was then transferred to a vacuum oven connected to the freeze drier and dried at 60° C. for 1 week at a pressure of 86 mTorr. One tablet was removed and tested for appearance, in vitro dissolution, HPLC purity and HPLC assay (T 1 week at 60° C.). The remaining tablets were kept in the blister pack in a sealed plastic bag containing a 10 g silica gel packet designed to protect an area of 91.5 cubic inch from moisture. The bags are stored both at ambient and 60° C. for long term stability testing.

Dipivefrin HCl ODT 2.5 mg

Dipivefrin HCl (33.2 mg) was dissolved in 7.00 g of the diluent solution to obtain the lyo solution. The lyo solution (535 µl) was then dispensed into each pocket of a blister pack with a diameter of 13 mm and a depth of 3 mm resulting in a dose of 5.0 mg per tablet. The tablet blister pack was then placed on top of dry ice for one hour. The frozen tablets were freeze dried for 24 hr at ambient. One tablet was removed from the blister pack and tested for in vitro dissolution, HPLC purity and HPLC assay (T0). The blister pack was then transferred to a vacuum oven connected to the freeze drier and dried at 60° C. for 1 week at a pressure of 86 mTorr. One tablet was removed and tested for appearance, in vitro dissolution, HPLC purity and HPLC assay (T 1 week at 60° C.). The remaining tablets were kept in the blister pack in a sealed plastic bag containing a 10 g silica gel packet designed to protect an area of 91.5 cubic inch from moisture. The bags are stored both at ambient and 60° C. for stability testing.

The stability data are summarized in Tables 5.1 and 5.2. As the data shown, at 60° C. under high vacuum, both the 5 mg and 2.5 mg strength dipivefrin HCl ODT showed no change in appearance, in vitro dissolution, HPLC purity and assay after 1 week. Since the main degradation pathway of dipivefrin is partial ester hydrolysis, without wishing to be bound by theory, the extraordinary stability of the dipivefrin ODTs at 60° C. is due to the absence of moisture under high vacuum. However, due to the highly porous nature of lyophilized tablets, the dipivefrin HCl ODTs can absorb some moisture quickly from the air during their removal from the vacuum oven. This is consistent with the accelerated hydrolytic degradation observed in week 2 and apparent slowing down between weeks 2-4 possibly due to the decrease in water content after week 2.

TABLE 5.1

Stability of dipivefrin HCl ODT 5 mg, stored in blister pack in a sealed plastic bag with silica gel packet at 60° C.

| Time point | | Initial | 1 week | 2 week | 4 week | 6 week | 8 week |
|---|---|---|---|---|---|---|---|
| Tablet appearance | | white | white | white | white | white | white |
| In vitro dissolution time (second) | | 1.10 | 2.20 | 1.22 | 1.69 | 1.70 | 1.40 |
| HPLC (assay % of dipivefrin HCl) | | 101.60 | 103.40 | 97.80 | 94.30 | 95.9 | 97.6 |
| HPLC (area %) | Relative Retention Time (RRT) | | | | | | |
| Dipivefrin | 1.000 | 99.77 | 99.76 | 98.66 | 97.64 | 96.40 | 95.07 |
| 3- or 4-monopivaloylepinephrine | 0.701 | 0.08 | 0.13 | 0.42 | 0.74 | 1.03 | 1.45 |
| 4- or 3-monopivaloylepinephrine | 0.773 | 0.15 | 0.16 | 0.51 | 0.90 | 1.31 | 1.77 |
| 4-[(methylamino)acetyl]-1,2-phenylene dipivalate | 1.036 | ND | ND | 0.41 | 0.72 | 1.26 | 1.71 |

TABLE 5.2

Stability of dipivefrin HCl ODT 2.5 mg, stored in blister pack in a sealed plastic bag with silica gel packet at 60° C.

| Time point | | Initial | 1 week | 2 week | 4 week | 6 week | 8 week |
|---|---|---|---|---|---|---|---|
| Tablet appearance | | white | white | white | white | White | White |
| In vitro dissolution time (second) | | 1.20 | 1.76 | 2.01 | 1.59 | 1.69 | 1.30 |
| HPLC (assay % of dipivefrin HCl) | | 100.1 | 103.2 | 98.0 | 96.7 | 95.2 | 97.1 |
| HPLC (area %) | Relative Retention Time (RRT) | | | | | | |
| Dipivefrin | 1.000 | 99.74 | 99.84 | 98.17 | 98.07 | 97.28 | 96.78 |
| 3- or 4-monopivaloylepinephrine | 0.701 | 0.09 | 0.10 | 0.33 | 0.59 | 0.86 | 1.15 |
| 4- or 3-monopivaloylepinephrine | 0.773 | 0.17 | 0.07 | 0.21 | 0.68 | 0.96 | 0.95 |
| 4-[(methylamino)acetyl]-1,2-phenylene dipivalate | 1.036 | ND | ND | 0.28 | 0.66 | 0.90 | 1.12 |

Example 6. Incubation of Dipivefrin HCl ODT in Fresh Human Saliva at 37° C.

This example demonstrates that dipivefrin HCl formulated as orally disintegrating tablets does not undergo significant hydrolysis in the oral cavity, in the short period of time which is typical for the administration of orally disintegrating tablets.

A dipivefrin HCl lyo solution having a composition listed in Table 6.1 below was lyophilized in a blister pack (0.560 ml/pocket) to obtain dipivefrin HCl ODT 25 mg strength as described in Example 3. The tablets were elegant with good strength for manual handling and in vitro dissolution time of 26 seconds in simulated saliva at 37° C.

About one quarter of the tablet was dissolved and incubated in 1 ml fresh human saliva at 37° C. for 11 min. An aliquot was diluted with deionized water, filtered through a 0.2 micrometer (μm) Nylon syringe filter and injected into HPLC. The analysis showed presence of about 13% epinephrine after incubation in saliva. In a separate experiment, about one quarter of the same tablet was incubated in 1 ml fresh human saliva at 37° C. for 3 min and HPLC showed no detectable epinephrine after the incubation.

TABLE 6.1

| Ingredient | % wt/wt. of water | Batch size (g) |
|---|---|---|
| Dipivefrin HCl | 5.00 | 0.125 |
| Gelatin | 3.00 | 0.075 |
| D-Mannitol | 1.00 | 0.025 |

TABLE 6.1-continued

| Ingredient | % wt/wt. of water | Batch size (g) |
|---|---|---|
| Glycine | 1.00 | 0.025 |
| PVP K30 | 1.00 | 0.025 |
| Citric acid | 1.00 | 0.025 |
| Deionized water | | 2.500 |
| Total | | 2.800 |

Example 7. Preparation of Dipivefrin HCl ODT 63.5 mg for Pharmacokinetics Study in Dogs A dipivefrin HCl lyo solution having a composition listed in Table 7.1 below was lyophilized in a blister pack (0.594 ml/pocket) to obtain dipivefrin HCl ODT 63.5 mg as described in Example 1. The tablet weight was 90.95±1.88 mg (SD, N=9).

TABLE 7.1

Composition of dipivefrin HCl lyo solution for the preparation of dipivefrin HCl ODT 63.5 mg

| Ingredient | % wt/wt. of water | Batch size (g) |
|---|---|---|
| Dipivefrin HCl | 12.7 | 0.6352 |
| Gelatin | 2 | 0.100 |
| D-Mannitol | 1 | 0.050 |
| Glycine | 1 | 0.050 |
| PVP K30 | 1 | 0.050 |
| Citric acid | 0.5 | 0.025 |
| Sucralose | 0.5 | 0.025 |
| Deionized water |  | 5.000 |
| Total |  | 5.935 |

Example 8. Preparation of Dipivefrin HCl ODT 5.0 Mg for Pharmacokinetics Study in Dogs A dipivefrin HCl lyo solution having a composition listed in Table 8.1 below was lyophilized in a blister pack (0.535 ml/pocket) to obtain dipivefrin HCl ODT 5.0 mg as described in Example 1. The tablets were white and had elegant appearance with pleasant taste. Weight: 34.97±0.42 mg (SD, N=9). In vitro dissolution time in simulated saliva at 37° C.: 4.90 seconds.

TABLE 8.1

Composition of dipivefrin HCl lyo solution for the preparation of dipivefrin HCl ODT 5 mg

| Ingredient | % wt/wt. of water | Batch size (g) |
|---|---|---|
| Dipivefrin HCl | 1 | 0.050 |
| Gelatin | 2 | 0.100 |
| D-Mannitol | 1 | 0.050 |
| Glycine | 1 | 0.050 |
| PVP K30 | 1 | 0.050 |
| Citric acid | 0.5 | 0.025 |
| Sucralose | 0.5 | 0.025 |
| Deionized water |  | 5.000 |
| Total |  | 5.350 |

Example 9. Pharmacokinetic Studies of Dipivefrin HCl ODT after Single Oral Administration in Dogs (N=3)

Pharmacokinetics of dipivefrin HCl was evaluated in dogs in a three leg cross-over design according to Table 9.3 below. Four days prior to study initiation, 1 mL of whole blood was collected from four (n=4) non-naïve male Beagle dogs, aged 1.5-6.5 years and ranging from 9.8 to 10.8 kilograms in weight, into 4 chilled tubes containing $K_2$EDTA (dipotassium EDTA). The blood was processed to plasma and plasma cholinesterase activity was assayed according to the Ellman method using acetylthiocholine iodide as the substrate (Ellman, G. L. et al Biochemical Pharmacology, 1961, volume 7, page 88-95). The assay results are summarized in Table 9.1. Based on the plasma cholinesterase activity assay results, the first three dogs with highest plasma cholinesterase activity were selected for the PK study.

TABLE 9.1

| dog # | Plasma cholinesterase activity (U/L) |
|---|---|
| 1 | 1408.3 |
| 2 | 1389.2 |
| 3 | 1441.4 |
| 4 | 1125.4 |

U/L: micromoles per minute per liter (μmol/min/L)

Dogs were housed one per cage and identified by ear tags and cage labels. The animals were healthy at the start of the study. Primary enclosures were as specified in the USDA Animal Welfare Act (9 CFR, Parts 1, 2, and 3) and as described in the Guide for Care and Use of Laboratory Animals (ILAR publication, 2011, National Academy Press). Animals were fasted for a minimum of 12 hours prior to dosing and returned 4 hours post dose; Water was supplied ad libitum to the animals.

Dosing occurred at 0 hours on the appropriate day in accordance with the Study Design table (Table 9.3). The first leg of epinephrine IM 0.3 mg (Composition shown in Table 9.2), standard care for anaphylaxis, is included as a control. The intramuscular dose was administered via 25 gauge needle and syringe into the lateral aspect of the left or right thigh. The dosing site was clipped free of hair and cleaned with alcohol prior to dosing. The orally disintegrating tablets were dosed by placing one tablet on the tongue of the dog. The muzzle was gently held closed for 1-2 minutes. After this period, the mouth was opened to observe that the tablet had completely dissolved.

TABLE 9.2

| Epinephrine IM 0.3 mg composition | |
|---|---|
| Ingredient | Amount |
| Epinephrine | 25.0 mg |
| Sodium chloride | 150.0 mg |
| Sodium metabisulfite | 41.75 mg |
| 1N HCl | 150 μl |
| Water for injection | q.s to 25.0 ml |

TABLE 9.3

| Study design (crossover) | | | | | |
|---|---|---|---|---|---|
| Leg # | Test Article Formulation | Dose Route | N= | Dose | Time points |
| 1 | Epinephrine solution | IM | 3 | 0.3 ml/animal | Pre-dose, 5, 10, 15, 20, 30, 40 min, 1, 1.5, 2, and 3 hours post dose |

TABLE 9.3-continued

Study design (crossover)

| Leg # | Test Article Formulation | Dose Route | N= | Dose | Time points |
|---|---|---|---|---|---|
| | Minimum 7 Day Washout | | | | |
| 2 | Dipivefrin HCl orally disintegrating tablet, 63.5 mg (equivalent to 57.6 mg dipivefrin freebase) of Example 7 | Orally disintegrating tablet | 3 | 1 tablet/animal | Pre-dose, 5, 10, 15, 20, 30, 40 min, 1, 1.5, 2 and 3 hours post dose |
| | Minimum 7 Day Washout | | | | |
| 3 | Dipivefrin HCl orally disintegrating tablet, 5 mg (equivalent to 4.5 mg dipivefrin freebase) of Example 9 | Orally disintegrating tablet | 3 | 1 tablet/animal | Pre-dose, 5, 10, 15, 20, 30, 40 min, 1, 1.5, 2 and 3 hours post dose |

Whole blood samples (~0.5 to 1 mL) were collected from the dog's jugular vein via direct venipuncture at the appropriate time point and placed into $K_2EDTA$ tubes as the anticoagulant. Blood samples were centrifuged at a temperature of 4° C. at 3000 g for 5 minutes. All samples were maintained chilled throughout processing. Plasma samples (250 μL) were aliquoted into 50 uL of 6% wt sodium metabisulfite solution in an eppendorf tube, and placed in a freezer set to maintain ~−70° C. until shipment in dry ice to the Keystone Bioanalytical for analysis of plasma concentrations of epinephrine.

The PK analysis results of dipivefrin HCl in dogs were summarized below (Table 9.4). The statistical analyses were performed using one-way analysis of variance (ANOVA) followed by Turkey's multiple comparisons test. All statistical analyses were performed using Prism 7.0 (GraphPad Software, San Diego, Calif.).

TABLE 9.4

Summary of PK analysis results in beagle dogs (data presented as mean ± standard error of the mean (SEM)

| Test articles | Dose | $C_{max}$ (ng/ml) | $T_{max}$ (min) | $AUC_{last}$ (ng min/ml) |
|---|---|---|---|---|
| Dipivefrin HCl orally disintegrating tablet | 63.5 mg | 46.60 ± 11.22 | 16.7 ± 3.3 | 2325.72 ± 459.60 |
| Dipivefrin HCl orally disintegrating tablet | 5.0 mg | 6.10 ± 2.65 | 30.0 ± 5.8 | 289.16 ± 76.14 |
| Epinephrine IM | 0.3 mg | 3.01 ± 1.43 | 25.0 ± 17.6 | 147.37 ± 39.41 |

$C_{max}$: maximum plasma concentration (mean±SEM of individual dog Cmax values); Tmax: time at which maximum plasma epinephrine concentration was achieved (mean±±SEM of individual dog Tmax values); $AUC_{0-last}$: area under the plasma concentration versus time curve (mean±SEM of individual dog AUC values). $T_{max}$ is the time at which the highest peak epinephrine concentration occurred in each individual dog. $T_{max}$ is limited by experimental design because it is a discrete variable based on defined times of blood sampling.

Figure 1:
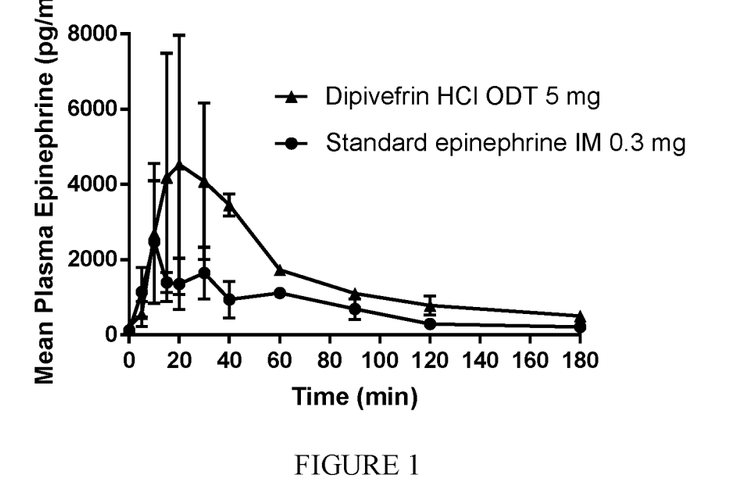
FIG. 1. Mean plasma epinephrine concentration vs time profiles after single oral dose of dipivefrin HCl orally disintegrating tablet 5 mg (refers to the weight of dipivefrin HCl salt) and single standard epinephrine intramuscular (IM) injection 0.3 mg in beagle dogs (cross over design, N=3).
Figure 2:
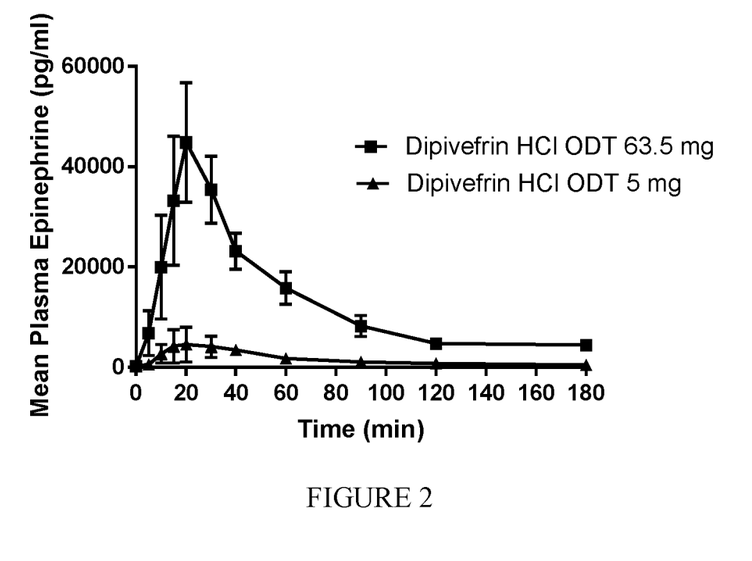
FIG. 2. Mean plasma epinephrine concentration vs time profiles after single oral dose of dipivefrin HCl orally disintegrating tablet 5 mg and 63.5 mg (refers to the weight of dipivefrin HCl salt) in beagle dogs (cross over design, N=3).

After administration of dipivefrin HCl orally disintegrating tablet to beagle dogs, plasma epinephrine concentration rises rapidly. The dipivefrin HCl orally disintegrating 5 mg tablet dose provided 2 times of $C_{max}$ and $AUC_{last}$ compared to the epinephrine standard IM 0.3 mg injection with comparable $T_{max}$. Dipivefrin HCl 63.6 mg produced significantly higher levels of epinephrine when compared to either the 5 mg dipivefrin HCl orally disintegrating tablet (p<0.05 for $C_{max}$ and p<0.01 for AUC) or the standard epinephrine IM 0.3 mg (p<0.01 for both $C_{max}$ and AUC). The mean plasma epinephrine vs time profiles are shown in FIG. 1 and FIG. 2. There is no significant difference in $T_{max}$ among all treatment groups (p>0.6). This example demonstrates that a dipivefrin HCl ODT can produce statistically equivalent levels of epinephrine in dogs as the standard epinephrine IM 0.3 mg, a drug of choice for emergency treatment of anaphylaxis.

Example 10. Pharmacokinetic Studies of Dipivefrin HCl ODT after Single Oral Administration in Dogs (N=6)

Pharmacokinetics of dipivefrin HCl was evaluated in six dogs in a three leg cross-over design according to Table 10.3 below. Four days prior to study initiation, 1 mL of whole blood was collected from seven (n=7) non-naïve male Beagle dogs, aged 1.5-6.5 years and ranging from 10.6 to 13.75 kilograms in weight, into 7 chilled tubes containing $K_2EDTA$. The blood was processed to plasma and plasma cholinesterase activity was assayed according to the Ellman method using acetylthiocholine iodide as the substrate (Ellman, G. L. et al Biochemical Pharmacology, 1961, volume 7, page 88-95). The assay results are summarized in Table 10.1. Based on the plasma cholinesterase activity assay results, the top six dogs with highest plasma cholinesterase activity were selected for the pharmacokinetic (PK) study.

TABLE 10.1

| dog # | Plasma cholinesterase activity (U/L) |
|---|---|
| 1 | 1395.7 |
| 2 | 1135.6 |
| 3 | 1330.0 |
| 4 | 1221.4 |
| 5 | 1248.9 |
| 6 | 1293.6 |
| 7 | 1140.7 |

Dogs were housed one per cage and identified by ear tags and cage labels. The animals were healthy at the start of the study. Primary enclosures were as specified in the USDA Animal Welfare Act (9 CFR, Parts 1, 2, and 3) and as described in the Guide for Care and Use of Laboratory Animals (ILAR publication, 2011, National Academy Press). Animals were fasted for a minimum of 12 hours prior to dosing and returned 4 hours post dose; Water was supplied ad libitum to the animals.

Dosing occurred at 0 hours on the appropriate day in accordance with the Study Design table (Table 10.2). The first leg of epinephrine IM 0.3 mg (Composition shown in Table 9.2), standard care for anaphylaxis, is included as a control. The intramuscular dose was administered via 25 gauge needle and syringe into the lateral aspect of the left or right thigh. The dosing site was clipped free of hair and cleaned with alcohol prior to dosing. The orally dissolving tablets (compositions shown in Table 10.2) were dosed by placing one tablet on the tongue of the dog. The muzzle was gently held closed for 1-2 minutes. After this period, the mouth was opened to observe that the tablet had completely dissolved.

TABLE 10.2

| Component | Amount (mg) in 1 tablet (Dipivefrin HCl ODT 1 mg) | Amount (mg) in 1 tablet (Dipivefrin HCl ODT 2.5 mg) |
|---|---|---|
| L-Dipivefrin HCl | 1.02 | 2.53 |
| Gelatin | 10.06 | 10.05 |
| Glycine | 10.06 | 10.05 |
| PVP K30 | 5.03 | 5.02 |
| Citric acid | 2.51 | 2.51 |
| Saccharin sodium | 2.51 | 2.51 |
| Tablet weight (mg) | 31.19 | 32.67 |

TABLE 10.3

Study design (crossover)

| Leg # | Test Article Formulation | Dose Route | N= | Dose | Time points |
|---|---|---|---|---|---|
| 1 | Epinephrine solution | IM | 6 | 0.3 ml/animal | Pre-dose, 5, 10, 15, 20, 30, 40 min, 1, 1.5, 2, and 3 hours post dose |
| | Minimum 7 Day Washout | | | | |
| 2 | Dipivefrin HCl ODT, 2.5 mg (equivalent to 2.3 mg dipivefrin freebase) | Orally disintegrating tablet | 6 | 1 tablet/animal | Pre-dose, 5, 10, 15, 20, 30, 40 min, 1, 1.5, 2 and 3 hours post dose |
| | Minimum 7 Day Washout | | | | |
| 3 | Dipivefrin HCl ODT, 1.0 mg (equivalent to 0.9 mg dipivefrin freebase) | Orally disintegrating tablet | 6 | 1 tablet/animal | Pre-dose, 5, 10, 15, 20, 30, 40 min, 1, 1.5, 2 and 3 hours post dose |

Whole blood samples (~0.5 to 1 mL) were collected from the dog's jugular vein via direct venipuncture at the appropriate time point and placed into $K_2$EDTA tubes as the anticoagulant. Blood samples were centrifuged at a temperature of 4° C. at 3000 g for 5 minutes. All samples were maintained chilled throughout processing. Plasma samples (250 μL) were aliquoted into 50 uL of 6% wt sodium metabisulfite solution in an eppendorf tube, and placed in a freezer set to maintain ~-70° C. until shipment in dry ice to the Keystone Bioanalytical for analysis of plasma concentrations of epinephrine.

The PK analysis results of dipivefrin HCl in dogs were summarized below (Table 10.4). The statistical analyses were performed using one-way ANOVA followed by Turkey's multiple comparisons test. All statistical analyses were performed using Prism 7.0 (GraphPad Software, San Diego, Calif.).

TABLE 10.4

Summary of PK analysis results in beagle dogs (data presented as mean ± SD)

| Test articles | Dose | $C_{max}$ (ng/ml) | $T_{max}$ (min) | $AUC_{0-last}$ (ng min/ml) |
|---|---|---|---|---|
| Dipivefrin HCl ODT | 2.5 mg | 4.6 ± 2.1 | 26.7 ± 17.2 | 189.0 ± 39.3 |
| Dipivefrin HCl ODT | 1.0 mg | 2.15 ± 0.78 | 31.7 ± 19.4 | 88.3 ± 10.9 |
| Epinephrine IM | 0.3 mg | 1.41 ± 0.79 | 19.2 ± 11.1 | 89.7 ± 15.8 |

$C_{max}$: maximum plasma concentration (mean±SD of individual dog $C_{max}$ values); $T_{max}$: time at which maximum plasma epinephrine concentration was achieved (mean±SD of individual dog $T_{max}$ values); $AUC_{0-last}$: area under the plasma concentration versus time curve (mean±SD of individual dog AUC values). $T_{max}$ is the time at which the highest peak epinephrine concentration occurred in each individual dog. $T_{max}$ is limited by experimental design because it is a discrete variable based on defined times of blood sampling.

Figure 3:
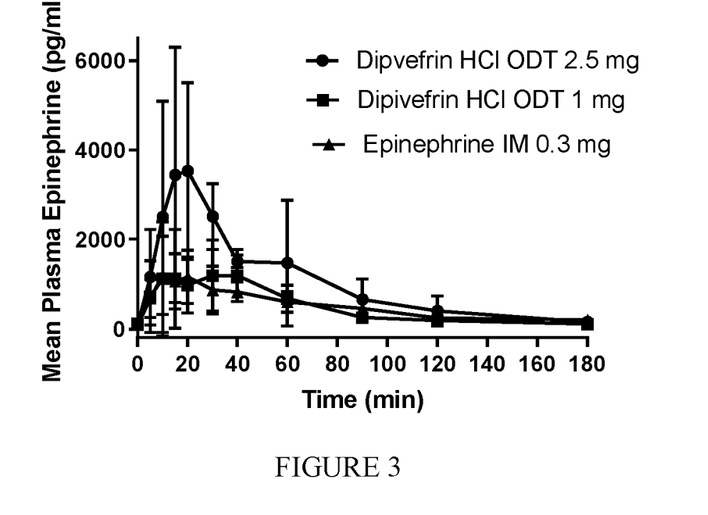
FIG. 3. Mean plasma epinephrine concentration vs time profiles after single oral dose of dipivefrin HCl orally disintegrating tablet 1.0 mg, 2.5 mg (refers to the weight of dipivefrin HCl salt) and single standard epinephrine IM injection 0.3 mg in beagle dogs (cross over design, N=6).

The mean plasma epinephrine vs time profiles are shown in FIG. 3. This example demonstrates that a dipivefrin HCl ODT can produce similar levels of epinephrine in dogs as the standard epinephrine IM 0.3 mg, a drug of choice for emergency treatment of anaphylaxis.

Example 11. Preparation of Dipivefrin HCl ODT Formulations of Flexible Tablet Sizes The purpose of this example is to illustrate the flexibility of the subject invention with regards to tablet size at the same strength. For example, smaller tablets can be conveniently made by simply increasing the amount of Active Pharmaceutical ingredient (API) while keeping the amount of inactive ingredients the same in the solution mix prior to lyophilization; higher API content requires smaller dose weight per blister pocket producing smaller tablets after freeze drying. The amount of each inactive ingredient can also be easily adjusted (Table 11.1).

TABLE 11.1

| Component | %(w/w) | | | | | | | | | | |
|---|---|---|---|---|---|---|---|---|---|---|---|
| L-Dipivefrin HCl | 0.50 | 0.50 | 0.19 | 0.40 | 0.50 | 0.40 | 0.50 | 0.40 | 0.50 | 0.40 | 0.50 |
| Gelatin | 0.47 | 0.94 | 1.88 | 1.88 | 1.88 | 2.82 | 2.82 | 3.76 | 3.76 | 4.70 | 4.70 |
| Glycine | 1.88 | 1.88 | 1.88 | 1.88 | 1.88 | 1.88 | 1.88 | 1.88 | 1.88 | 1.88 | 1.88 |
| PVP K30 | 0.94 | 0.94 | 0.94 | 0.94 | 0.94 | 0.94 | 0.94 | 0.94 | 0.94 | 0.94 | 0.94 |
| Citric acid | 0.47 | 0.47 | 0.47 | 0.47 | 0.47 | 0.47 | 0.47 | 0.47 | 0.47 | 0.47 | 0.47 |
| Saccharin sodium | 0.47 | 0.47 | 0.47 | 0.47 | 0.47 | 0.47 | 0.47 | 0.47 | 0.47 | 0.47 | 0.47 |
| Purified water, QS to | 100 | 100 | 100 | 100 | 100 | 100 | 100 | 100 | 100 | 100 | 100 |
| Dose weight/blister pocket (mg) | 200 | 200 | 535 | 250 | 200 | 250 | 200 | 250 | 200 | 250 | 200 |
| Tablet strength (dipivefrin freebase, mg) | 0.91 | 0.91 | 0.91 | 0.91 | 0.91 | 0.91 | 0.91 | 0.91 | 0.91 | 0.91 | 0.91 |
| Expected tablet weight (mg) | 9.46 | 10.40 | 31.19 | 15.10 | 12.28 | 17.45 | 14.16 | 19.80 | 16.04 | 22.15 | 17.92 |

What is claimed is:

1. A dipivefrin orally disintegrating tablet (ODT), comprising dipivefrin, or a pharmaceutically acceptable salt thereof, a binder, a matrix former, and a taste masking agent, wherein the tablet produces no detectable epinephrine when dissolved in fresh human saliva at 37° C. for 3 minutes, as determined by HPLC.

2. The ODT of claim 1, wherein the percent epinephrine is determined by HPLC, using the following conditions: C18 column, 3 μm, 100 mm×4.6 mm, temperature 30° C., 254 nm detection, 1.0 mL/minute flow rate, 10 microliter injection volume, elution gradient:
Solvent A is 0.1% Trifluoroacetic acid (TFA) in $H_2O$, Solvent B is 0.1% TFA in acetonitrile, and the gradient from 0 to 12 minutes is:

| Time (min) | Solvent A (%) | Solvent B (%) |
|---|---|---|
| 0 | 90 | 10 |
| 4 | 50 | 50 |
| 6 | 35 | 65 |
| 8 | 90 | 10 |
| 12 | 90 | 10. |

3. The ODT of claim 2, comprising 0.01 mg to 20 mg dipivefrin hydrochloride.

4. The ODT of claim 2, comprising 0.5 mg, 1.0 mg, 2.5 mg, or 5 mg dipivefrin hydrochloride.

5. The ODT of claim 2, wherein the total weight of the tablet is less than 50 mg.

6. The ODT of claim 2, comprising 10 to 70% binder (wt %), 5 to 50% matrix former (wt %), and 1 to 20% taste masking agent (wt %).

7. A dipivefrin hydrochloride orally disintegrating tablet (ODT), comprising not more than 63.5 mg dipivefrin hydrochloride, a binder, a matrix former, and a taste masking agent, wherein the ODT provides an epinephrine $T_{max}$ of less than 45 minutes and a plasma epinephrine $C_{max}$ of 0.1 to 50 ng/mL, when administered to a dog or human.

8. The ODT of claim 7, wherein the ODT contains not more than 5 mg of dipivefrin hydrochloride and provides a plasma level of epinephrine at 20 minutes after administration that is equal or greater than a plasma level of epinephrine provided by a US FDA-approved injectable epinephrine dosage form, comprising 0.5 mg, epinephrine 0.3 mg epinephrine, 0.15 mg epinephrine, or 0.1 mg epinephrine.

9. The ODT of claim 8, wherein the US FDA-approved injectable epinephrine dosage form is approved for intramuscular administration.

10. The ODT of claim 8, wherein the US FDA-approved injectable epinephrine dosage form is approved for subcutaneous administration.

11. The ODT of claim 2, wherein the dipivefrin is L-dipivefrin.

12. A dipivefrin orally disintegrating tablet (ODT) comprising dipivefrin hydrochloride and 9-53% gelatin (wt %), 20-40% glycine (wt %), 10-20% PVP K30 (wt %), 5-10% citric acid (wt %), and 5-10% saccharin sodium (wt %).

13. The ODT of claim 1, further comprising a permeation enhancer.

14. The ODT of claim 13, wherein the permeation enhancer is caprylic acid, oleic acid, polysorbate 80 (Polyethylene glycol sorbitan monooleate), menthol, ethylenediaminetetraacetic acid (EDTA), sodium edetate, cetylpyridinium chloride, sodium lauryl sulfate, citric acid, sodium desoxycholate, sodium deoxyglycolate, glyceryl oleate, L-lysine, or a combinations thereof.

15. A dipivefrin orally disintegrating tablet (ODT), comprising dipivefrin or a pharmaceutically acceptable salt thereof, a binder, a matrix former, a taste masking agent, and a penetration enhancer, wherein the tablet produces not more than 13 percent epinephrine when dissolved in fresh human saliva at 37° C. for 11 minutes, as determined by HPLC.

16. The ODT of claim 15, wherein the percent epinephrine is determined by HPLC, using the following conditions: C18 column, 3 μm, 100 mm×4.6 mm, temperature 30° C., 254 nm detection, 1.0 mL/minute flow rate, 10 microliter injection volume, elution gradient:
Solvent A is 0.1% Trifluoroacetic acid (TFA) in $H_2O$, Solvent B is 0.1% TFA in acetonitrile, and the gradient from 0 to 12 minutes is:

| Time (min) | Solvent A (%) | Solvent B (%) |
|---|---|---|
| 0 | 90 | 10 |
| 4 | 50 | 50 |
| 6 | 35 | 65 |
| 8 | 90 | 10 |
| 12 | 90 | 10. |

17. The ODT of claim 16, comprising 0.01 mg to 20 mg dipivefrin hydrochloride.

18. The ODT of claim 16, comprising 0.5 mg, 1.0 mg, 2.5 mg, or 5 mg dipivefrin hydrochloride, wherein the total weight of the tablet is less than 50 mg.

19. The ODT of claim 7, wherein the dipivefrin hydrochloride is L-dipivefrin hydrochloride.

20. The ODT of claim 12, wherein the dipivefrin hydrochloride is L-dipivefrin hydrochloride.

21. The ODT of claim 16, wherein the dipivefrin is L-dipivefrin hydrochloride.

\* \* \* \* \*